(12) United States Patent (10) Patent No.: US 9,983,170 B2
Onuma (45) Date of Patent: May 29, 2018

(54) ANALYSIS METHOD, ANALYSIS CHIP, AND ANALYSIS SYSTEM

(71) Applicant: ARKRAY, Inc., Kyoto-shi (JP)

(72) Inventor: Naotsugu Onuma, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days. days.

(21) Appl. No.: 14/849,966

(22) Filed: Sep. 10, 2015

(65) Prior Publication Data

US 2016/0077053 A1 Mar. 17, 2016

(30) Foreign Application Priority Data

Sep. 11, 2014 (JP) .................................. 2014-185071
Aug. 10, 2015 (JP) .................................. 2015-158129

(51) Int. Cl.
*G01N 27/447* (2006.01)
*G01N 27/453* (2006.01)
*G01N 33/72* (2006.01)
*B01L 3/00* (2006.01)

(52) U.S. Cl.
CPC .. *G01N 27/44791* (2013.01); *B01L 3/502715* (2013.01); *G01N 27/44743* (2013.01); *G01N 27/453* (2013.01); *G01N 33/721* (2013.01); *B01L 2200/10* (2013.01); *B01L 2300/0838* (2013.01); *B01L 2400/0421* (2013.01); *G01N 27/44756* (2013.01); *G01N 2333/805* (2013.01)

(58) Field of Classification Search
CPC ............. B01L 3/5027; B01L 3/502707; B01L 3/502715; B01L 3/50723; B01L 3/5023; B01L 3/502776; B01L 2400/0415–2400/0427; G01N 27/44791; G01N 27/44756–27/453; B81B 1/00–1/008
See application file for complete search history.

(56) References Cited

U.S. PATENT DOCUMENTS

| 2005/0006238 | A1* | 1/2005 | Jaffe ................ G01N 27/44791 204/450 |
| 2010/0116660 | A1* | 5/2010 | Tanaka ............. G01N 27/44791 204/452 |
| 2010/0181199 | A1 | 7/2010 | Sugiyama et al. |
| 2010/0258440 | A1* | 10/2010 | Sugiyama ............. B01D 57/02 204/451 |
| 2013/0312546 | A1* | 11/2013 | Wada ...................... B01L 3/021 73/864.11 |

FOREIGN PATENT DOCUMENTS

| JP | 11-337521 A | 10/1999 |
| WO | 2008/136465 A1 | 11/2008 |

OTHER PUBLICATIONS

Extended European Search Report dated Feb. 22, 2016 in corresponding EP Application No. 15183929.7.

* cited by examiner

*Primary Examiner* — Gurpreet Kaur
(74) *Attorney, Agent, or Firm* — Knobbe, Martens, Olson & Bear, LLP

(57) ABSTRACT

A method is provided for analyzing a sample using capillary electrophoresis. According to the method, an electrophoretic liquid filling step is performed for filling a capillary tube with an electrophoretic liquid. In an introducing step, a predetermined amount of sample is introduced to an introducing tank linked to the capillary tube. In a flow step, performed after the introducing step, the sample is caused to flow in the introducing tank, thereby generating a shear flow at a link portion between the capillary tube and the introducing tank. In an electrophoresis step, electrophoresis is performed in the capillary tube while the sample is continuously supplied.

3 Claims, 11 Drawing Sheets

ANALYSIS METHOD, ANALYSIS CHIP, AND ANALYSIS SYSTEM

BACKGROUND OF THE INVENTION

1. Field of the Invention

The present invention relates to an analysis method, an analysis chip, and an analysis system.

2. Description of Related Art

Conventionally, glycation degrees of various proteins are analyzed for checking the condition of a living body. In particular, the glycation degree of hemoglobin (Hb) in blood cells is regarded as an important indicator in diagnosis, treatment, and the like of diabetes because it reflects the history of previous blood glucose levels in a living body. HbA1c, which is a typical example of hemoglobin used as such an indicator, is HbA($\alpha 2\beta 2$) with glycated valine at the N-terminal of the $\beta$-chain.

Examples of a method for analyzing Hb include electrophoresis methods. JP H11-337521A discloses an analysis method using an analysis chip that includes a capillary tube and an auxiliary flow path orthogonal to the capillary tube. A sample retained at an intersection of the capillary tube and the auxiliary flow path is analyzed in the electrophoresis method. This configuration is used in order to perform an accurate analysis with a very small amount of sample. WO 2008/136465 describes an analysis method that continuously supplies a sample also during separation of the sample by electrophoresis, in order to reduce the size of a chip for use in an analysis using an electrophoresis method.

However, according to the configuration of JP H11-337521A, before electrophoresis in the capillary tube, the linking space between the capillary tube and the auxiliary flow path has to be filled with a sample by the application of a voltage to two electrodes arranged at both ends of the auxiliary flow path. According to the configuration of WO 2008/136465, before the start of an analysis using the electrophoresis method, an electrophoretic liquid in the capillary tube may leak into a sample storage tank or the like. This leakage may significantly lower the precision of the analysis result. If the electrophoretic liquid that has leaked is concentrated by drying before the sample is introduced, a region excessively containing the components of the electrophoretic liquid may be formed at a portion of the sample that is to be analyzed first. Also, the electrophoretic liquid and the sample may be mutually diffused, forming a region having an unclear component ratio of the solution.

SUMMARY OF THE INVENTION

The present invention has been proposed under the circumstances described above, and it is an object thereof to provide an analysis method, an analysis chip, and an analysis system capable of improving the analysis precision with a simpler configuration.

According to a first aspect of the present invention, there is provided a method for analyzing a sample using capillary electrophoresis. The method includes: an electrophoretic liquid filling step of filling a capillary tube with an electrophoretic liquid; an introducing step of introducing a predetermined amount of sample into an introducing tank linked to the capillary tube; a flow step of, after the introducing step, causing the sample to flow in the introducing tank, thereby generating a shear flow at a link portion between the capillary tube and the introducing tank; and an electrophoresis step of performing electrophoresis in the capillary tube while the sample is continuously supplied.

Preferably, the introducing tank is provided with two opening portions that are disposed opposite from each other with the link portion interposed between the two opening portions, and in the flow step, the sample is poured into and discharged from the two opening portions.

According to a second aspect of the present invention, there is provided with a disposable analysis chip for analyzing a sample using capillary electrophoresis. The analysis chip includes: an introducing tank into which a sample is introduced; a capillary tube linked to the introducing tank; a discharging tank linked to the capillary tube and opposite from the introducing tank; and a flow means for causing a predetermined amount of the sample introduced into the introducing tank to flow in the introducing tank.

Preferably, the flow means includes two opening portions provided on the introducing tank and disposed opposite from each other with a link portion between the introducing tank and the capillary tube being interposed between the two opening portions.

Preferably, the two opening portions are opened to face in a same direction.

According to a third aspect of the present invention, there is provided an analysis system includes: an analysis chip according to the above-mentioned second aspect; and an analysis device to which the analysis chip is set, where the analysis device includes an analysis portion for performing electrophoresis in the capillary tube while the sample is continuously supplied.

Preferably, the analysis device further includes a flow drive source that provides the flow means of the analysis chip with a driving force for generating a flow.

According to the present invention, the flow step mentioned above is performed, whereby a clearly-defined boundary is to form between the sample and the electrophoretic liquid at the link portion between the introducing tank and the capillary tube. In other words, the flow step ensures that a portion of the sample at or around the link portion (where the sample may be diluted, or the components of the electrophoretic liquid may be concentrated, or the sample may have an known component ratio) can be washed away by e.g., a shear flow produced in the flow step. As a result, the pure sample (suitable for the intended analysis) can be present at the link portion between the introducing tank and the capillary tube. Accordingly, the analysis precision can be improved with simpler arrangements than are conventionally possible.

Other features and advantages of the present invention will become more apparent from the detailed description given below with reference to the attached drawings.

DESCRIPTION OF THE PREFERRED EMBODIMENT

Hereinafter, preferred embodiments of the present invention will be specifically described with reference to the drawings.

Figure 1:
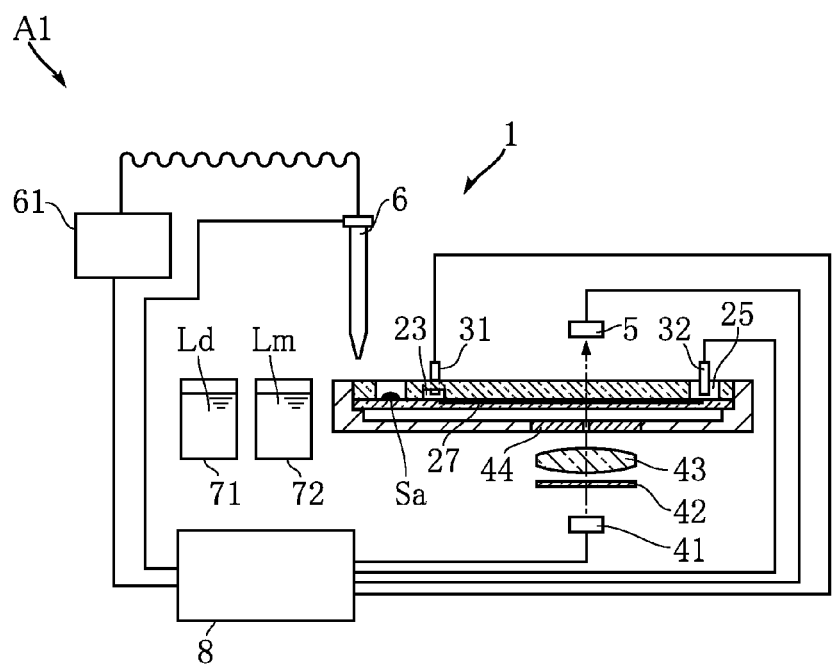
FIG. 1 is a schematic system view showing an analysis system according to a first embodiment of the present invention.

FIG. 1 shows an analysis system according to a first embodiment of the present invention. The analysis system A1 of this embodiment includes an analysis device 1 and an analysis chip 2. The analysis system A1 is a system that carries out an analysis method on a sample Sa using an electrophoresis method. Although there is no particular limitation on the kind of the sample Sa, this embodiment uses blood collected from a human body, as an example. Of the components contained in the sample Sa, the component to be analyzed is referred to as the "analysis component" below.

Examples of the analysis component include hemoglobin (Hb), albumin (Alb), globulin ($\alpha$1, $\alpha$2, $\beta$, $\gamma$ globulin), fibrinogen, and the like. Examples of the hemoglobin include normal hemoglobin (HbA0), glycated hemoglobin, modified hemoglobin, fetal hemoglobin (HbF), and the like. Examples of the glycated hemoglobin include hemoglobin A1a (HbA1a), hemoglobin A1b (HbA1b), hemoglobin A1c (HbA1c), GHbLys, and the like. Examples of the hemoglobin A1c include stable HbA1c (s-HbA1c), unstable HbA1c (l-HbA1c), and the like. Examples of the modified hemoglobin include carbamylated Hb, acetylated Hb, and the like. In the description below, a case in which the analysis component is Hb will be described as an example.

Figure 2:
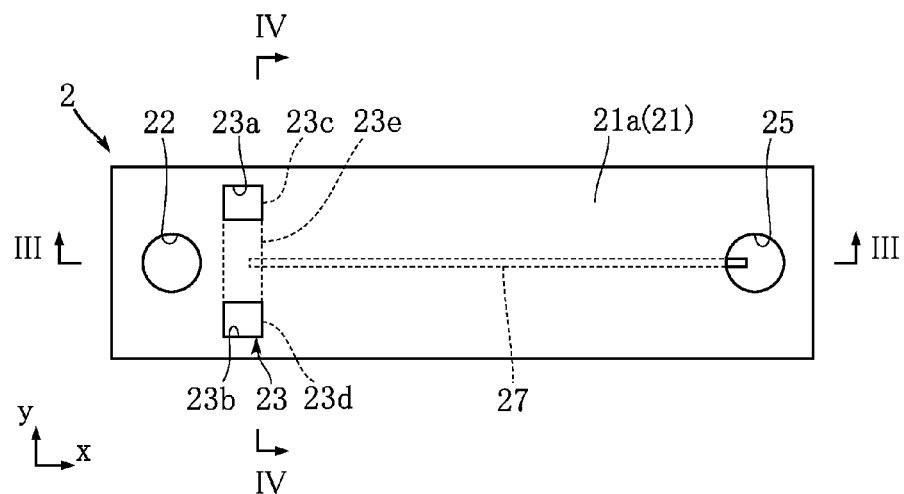
FIG. 2 is a plan view showing an analysis chip for use in the analysis system in FIG. 1.
Figure 3:
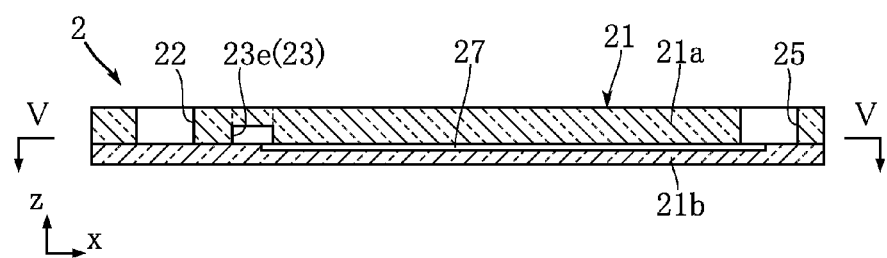
FIG. 3 is a cross-sectional view taken along the line III-III in FIG. 2.
Figure 4:
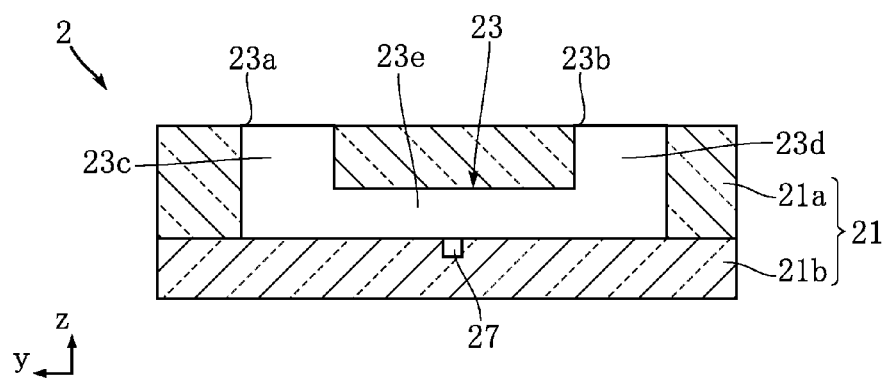
FIG. 4 is a cross-sectional view taken along the line IV-IV in FIG. 2.
Figure 5:
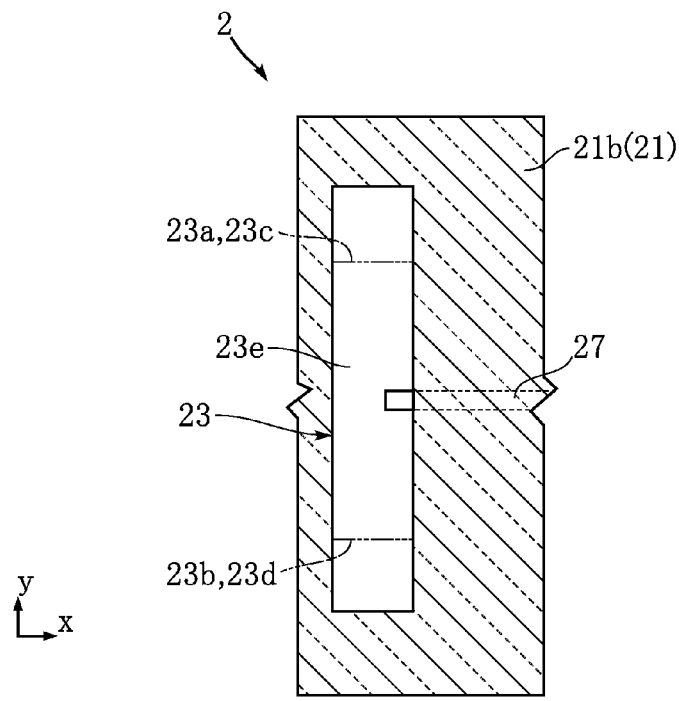
FIG. 5 is an enlarged cross-sectional view of the main portions taken along the line V-V in FIG. 3.

The analysis chip 2 is configured to hold the sample Sa and provides an analysis field in which a required analysis is to be performed with respect to the sample Sa when the analysis chip 2 is set in the analysis device 1. In this embodiment, the analysis chip 2 is configured as a so-called disposable analysis chip that is intended to be disposed of after analysis is performed once or a designated number of times. As shown in FIGS. 2 to 5, the analysis chip 2 includes a main body 21, which is provided with a mixing tank 22, an introducing tank 23, a discharging tank 25 and a capillary tube 27. FIG. 2 is a plan view of the analysis chip 2. FIG. 3 is a cross-sectional view taken along the line III-III in FIG. 2, and FIG. 4 is a cross-sectional view taken along the line IV-IV in FIG. 2. FIG. 5 is an enlarged cross-sectional view of the main portions taken along the line V-V in FIG. 3. In the drawings, the x direction corresponds to the direction in which the capillary tube 27 extends, the y direction corresponds to the width direction of the capillary tube 27, and the z direction corresponds to the depth direction of the capillary tube 27 and the introducing tank 23.

The main body 21 is a base for the analysis chip 2. The main body 21 may be made of, for example, glass, molten silica, plastic, and the like. In this embodiment, the main body 21 has a configuration in which an upper portion 21a and a lower portion 21b are bonded to each other. Note that a configuration is also possible in which the main body 21 is processed from a single piece of a material.

The mixing tank 22 is an example of a mixing portion that performs a mixing step (described later) of mixing the sample Sa and a diluting liquid Ld. The mixing tank is formed, for example, as a through-hole that is formed through the upper portion 21a of the main body 21.

The introducing tank 23 is a tank to which a mixed sample Sm obtained by the mixing step in the mixing tank 22 is to be introduced. The introducing tank 23 of this embodiment, having two opening portions 23a and 23b, is made up of a vertical hole portion 23c, a vertical hole portion 23d, and a lateral hole portion 23e. The two opening portions 23a and 23b are spaced away in the y direction, and both opening portions are opened in the direction of the arrow in the z direction. As described later in detail, the two opening portions 23a and 23b serve as "flow means" (or at least a part of the flow means) that is used for producing a required flow in the introducing tank 23. Specifically, after the introduction of a predetermined amount of mixed sample Sm to the introducing tank 23 is completed, driving force from a flow drive source of the analysis device 1 is provided through the opening portions so as to cause the mixed sample Sm to flow in the introducing tank 23. The "sample" regarding the present invention refers to a liquid that is to be analyzed in the analysis method, and, in this embodiment, refers to the mixed sample Sm that is to be introduced to the introducing tank 23. Note that not only the mixed sample Sm obtained by the mixing step but also a sample subjected to other processing or the sample Sa not subjected to any processing may be introduced to the introducing tank 23 as a sample in the analysis method of the present invention.

The vertical hole portion 23c is linked to the opening portion 23a, and the vertical hole portion 23d is linked to the opening portion 23b. The vertical hole portion 23c and the vertical hole portion 23d extend in the direction opposite from the arrow in the z direction. The lateral hole portion 23e is a portion not exposed to the outside, linking portions near the lower ends in the z direction of the vertical hole portion 23c and the vertical hole portion 23d, and extending in the y direction. In this embodiment, the capillary tube 27 is linked to a portion near the middle in the y direction of the lateral hole portion 23e.

The discharging tank 25 is a tank that is positioned downstream of an electroosmotic flow in the electrophoresis method. The discharging tank 25 is formed, for example, as a through-hole that is formed through the upper portion 21a of the main body 21.

The capillary tube 27 links the introducing tank 23 and the discharging tank 25, and an electroosmotic flow in the electrophoresis method is generated in this capillary tube 27. The capillary tube 27 is formed, for example, as a groove that is formed in the lower portion 21b of the main body 21. Note that, in the main body 21, a recess portion and the like may be formed for facilitating irradiation of the capillary tube 27 with light and emission of light that has been transmitted through the capillary tube 27. There is no particular limitation on the size of the capillary tube 27, but, for example, the width is 25 µm to 100 µm, the depth is 25 µm to 100 µm, and the length is 5 mm to 150 mm. The size of the entire analysis chip 2 is set as appropriate according to the size of the capillary tube 27, the size and the arrangement of the mixing tank 22, the introducing tank 23, and the discharging tank 25, and the like.

In this embodiment, as shown in FIGS. 3 and 4, the vertical hole portion 23c, the vertical hole portion 23d, and the lateral hole portion 23e are formed as through-holes and a recess portion formed in the upper portion 21a of the main body 21. As shown in FIG. 4, the capillary tube 27 is linked, from below in the z direction, to a portion near the middle in the y direction of the lateral hole portion 23e. The dimensions in the x direction and in the y direction of the lateral hole portion 23e are significantly larger than the dimensions in the x direction and in the y direction of the opening portion of the capillary tube 27 exposed to the lateral hole portion 23e.

The analysis device 1 analyzes the sample Sa in a state where the analysis chip 2 to which the sample Sa was added dropwise is set in the analysis device 1. The analysis device 1 includes electrodes 31 and 32, a light source 41, an optical filter 42, a lens 43, a slit 44, a detector 5, an injector 6, a pump 61, a diluting liquid tank 71, an electrophoretic liquid tank 72, and a control portion 8.

The electrode 31 and the electrode 32 are for applying a predetermined voltage to the capillary tube 27 in the electrophoresis method. The electrode 31 is inserted into the introducing tank 23 of the analysis chip 2, and the electrode 32 is inserted into the discharging tank 25 of the analysis chip 2. There is no particular limitation on a voltage applied to the electrode 31 and the electrode 32, and examples thereof include a range of 0.5 kV to 20 kV.

The light source 41 is a portion that emits light for light absorbance measurement in the electrophoresis method. The light source 41 includes, for example, an LED chip that emits light in a predetermined wavelength range. The optical filter 42 is for attenuating light having a predetermined wavelength, of the light from the light source 41, while allowing light having the other wavelengths to be transmitted therethrough. The lens 43 is for converging light that has been transmitted through the optical filter 42, on an analysis point of the capillary tube 27 of the analysis chip 2. The slit 44 is for removing unnecessary light that may cause scattering or the like, of the light that has been converged by the optical filter 42.

The detector 5 is for receiving light that has been transmitted through the capillary tube 27 of the analysis chip 2, and includes, for example, a photodiode, a photo IC, or the like.

The injector 6 is for injecting a desired amount of diluting liquid Ld, electrophoretic liquid Lm, or mixed sample Sm, and includes, for example, a nozzle. The injector 6 can be freely moved between a plurality of predetermined positions in the analysis device 1 by an unshown drive mechanism. The pump 61 functions as a suction source and an ejection source into and from the injector 6. Furthermore, the pump 61 may be used as a suction source and an ejection source into and from unshown ports provided in the analysis device 1. The ports are used for filling an electrophoretic liquid Lm and the like. Note that a dedicated pump other than the pump 61 may be provided. The pump 61 corresponds to an example of the flow drive source in the present invention. Furthermore, the above-described dedicated pump other than the pump 61 may be used as the flow drive source.

The diluting liquid tank 71 is a tank for storing the diluting liquid Ld. The diluting liquid tank 71 may be a tank permanently installed in the analysis device 1, or may be a container set in the analysis device 1 in a state of containing a predetermined amount of diluting liquid Ld. The electrophoretic liquid tank 72 is a tank for storing the electrophoretic liquid Lm. The electrophoretic liquid tank 72 may be a tank permanently installed in the analysis device 1, or may be a container set in the analysis device 1 in a state of containing a predetermined amount of electrophoretic liquid Lm.

The diluting liquid Ld is mixed with the sample Sa to form a mixed sample Sm. There is no particular limitation on the main component of the diluting liquid Ld. Examples thereof include water and physiological saline, and preferable examples thereof include a liquid having components similar to those of the electrophoretic liquid Lm (described later). The diluting liquid Ld is obtained by adding an anionic group-containing compound to the main component. Examples of the anionic group-containing compound include an anionic group-containing polysaccharide. The anionic group-containing polysaccharide is, for example, at least one polysaccharide selected from the group consisting of sulfated polysaccharides, carboxylated polysaccharides, sulfonated polysaccharides, and phosphorylated polysaccharides. The carboxylated polysaccharide is preferably alginic acid or a salt thereof (e.g., sodium alginate). The sulfated polysaccharide is, for example, chondroitin sulfate. There are seven types of chondroitin sulfates A, B, C, D, E, H, and K and any of them may be used. In the description below, a case in which the diluting liquid Ld is obtained by adding chondroitin sulfate to the main component that is the same as the electrophoretic liquid Lm will be described as an example. The anionic group-containing compound (chondroitin sulfate) has a concentration of, for example, 0.01 to 5% by weight.

The electrophoretic liquid Lm is a medium with which the discharging tank 25 and the capillary tube 27 are filled, and in which an electroosmotic flow in the electrophoresis method is generated, in the analysis step in the electrophoresis method. There is no particular limitation on the electrophoretic liquid Lm, but preferable examples thereof include those using an acid. Examples of the acid include citric acid, maleic acid, tartaric acid, succinic acid, fumaric acid, phthalic acid, malonic acid, and malic acid. The electrophoretic liquid Lm preferably contains a weak base. Examples of the weak base include arginine, lysine, histidine, tris, and the like. The electrophoretic liquid Lm has a pH of, for example, 4.5 to 6. Examples of the buffer type of the electrophoretic liquid Lm include MES, ADA, ACES, BES, MOPS, TES, HEPES, and the like. The anionic group-containing compound as in the description of the diluting liquid Ld is added also to the electrophoretic liquid Lm. The anionic group-containing compound (chondroitin sulfate) has a concentration of, for example, 0.01 to 5% by weight.

The control portion 8 controls various portions in the analysis device 1. The control portion 8 includes, for example, a CPU, a memory, an interface, and the like.

Figure 6:
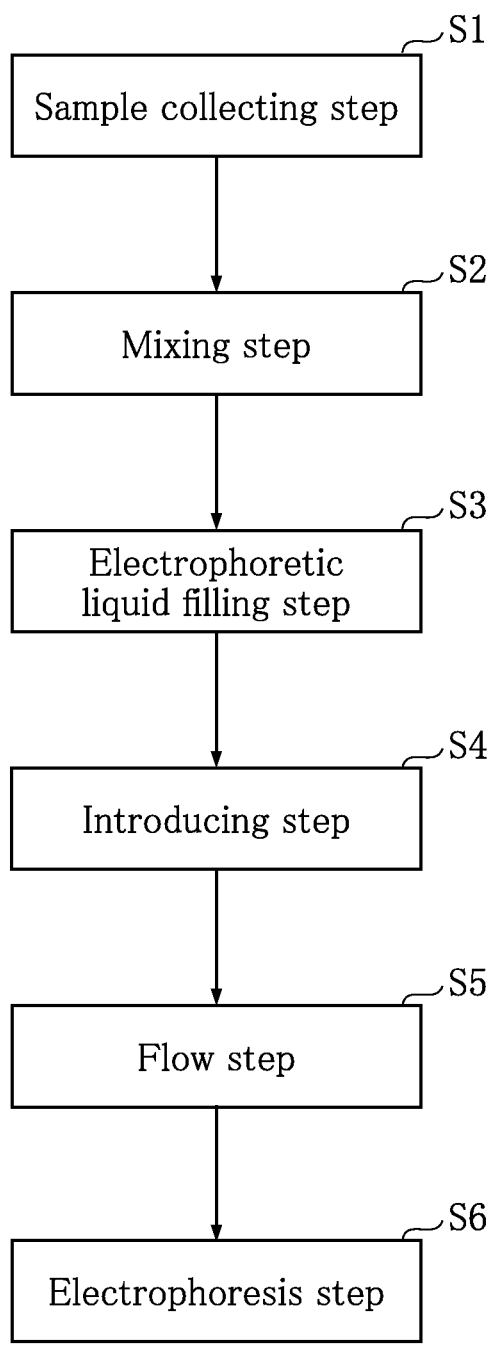
FIG. 6 is a flowchart showing an analysis method according to the first embodiment of the present invention.

Next, the analysis method according to the first embodiment of the present invention using the analysis system A1 will be described below. FIG. 6 is a flowchart showing an analysis method of this embodiment. This analysis method includes a sample collecting step S1, a mixing step S2, an electrophoretic liquid filling step S3, an introducing step S4, a flow step S5, and an electrophoresis step S6.

<Sample Collecting Step S1>

Figure 7:
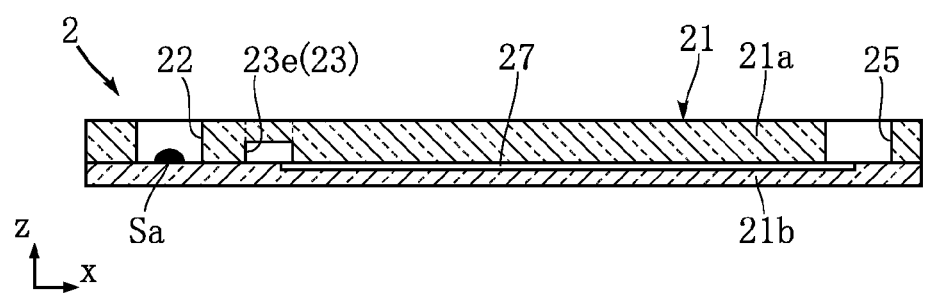
FIG. 7 is a cross-sectional view showing the analysis method in FIG. 6.

First, a sample Sa is prepared. In this embodiment, the sample Sa is blood collected from a human body. The blood may be whole blood, or may be hemolyzed blood subjected to hemolysis treatment, for example. Then, as shown in FIG. 7, the analysis chip 2 to which the sample Sa was injected is set in the analysis device 1.

<Mixing Step S2>

Figure 8:
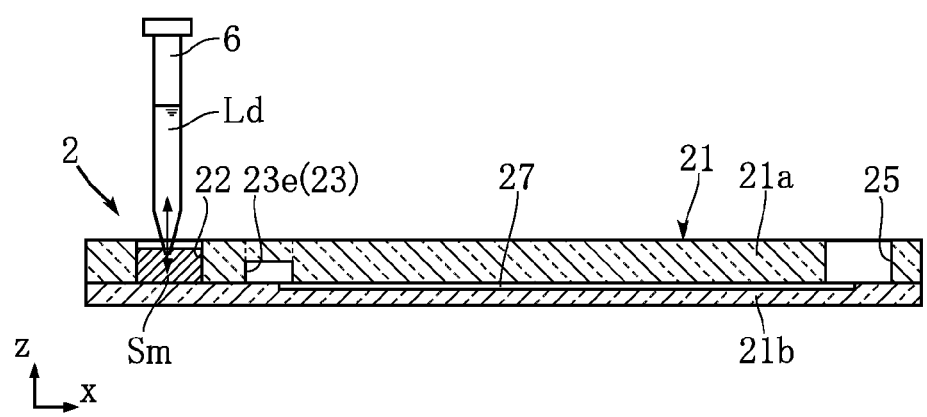
FIG. 8 is a cross-sectional view showing the analysis method in FIG. 6.

Then, the sample Sa and the diluting liquid Ld are mixed. Specifically, as shown in FIG. 7, a predetermined amount of sample Sa has been added dropwise to the mixing tank 22 of the analysis chip 2. Then, a predetermined amount of diluting liquid Ld in the diluting liquid tank 71 is sucked by the injector 6, and, as shown in FIG. 8, the predetermined amount of diluting liquid Ld is injected to the mixing tank 22 of the analysis chip 2. The diluting liquid Ld is repeatedly sucked into and ejected from the injector 6, using the pump 61 as the suction source and the ejection source. Accordingly, the sample Sa and the diluting liquid Ld are mixed in the mixing tank 22, so that a mixed sample Sm is obtained. The sample Sa and the diluting liquid Ld may be mixed using a method other than that performs the suction and ejection into and from the injector 6. With the mixing step S2, a complex in which the analysis component Hb and chondroitin sulfate are bound to each other is generated.

<Electrophoretic Liquid Filling Step S3>

Figure 9:
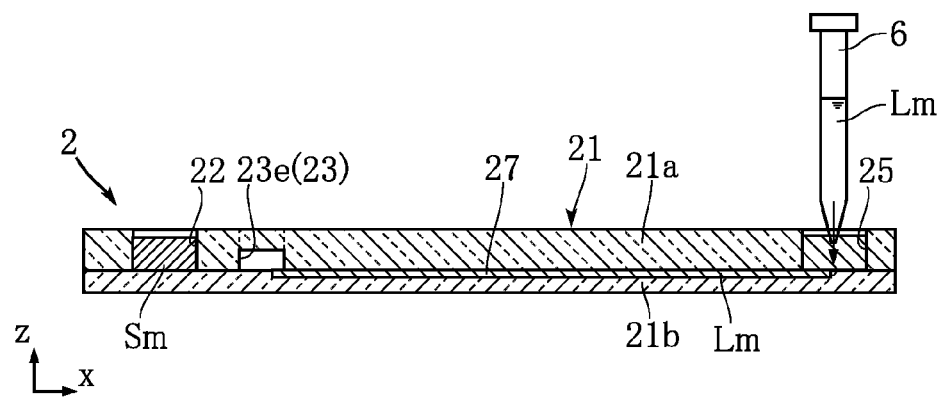
FIG. 9 is a cross-sectional view showing the analysis method in FIG. 6.

Then, a predetermined amount of electrophoretic liquid Lm in the electrophoretic liquid tank 72 is sucked by the injector 6, and, as shown in FIG. 9, the predetermined amount of electrophoretic liquid Lm is injected to the discharging tank 25 of the analysis chip 2. Then, for example, using a method that performs as appropriate suction and ejection through ports as described above, the discharging tank 25 and the capillary tube 27 are filled with the electrophoretic liquid Lm.

<Introducing Step S4>

Figure 10:
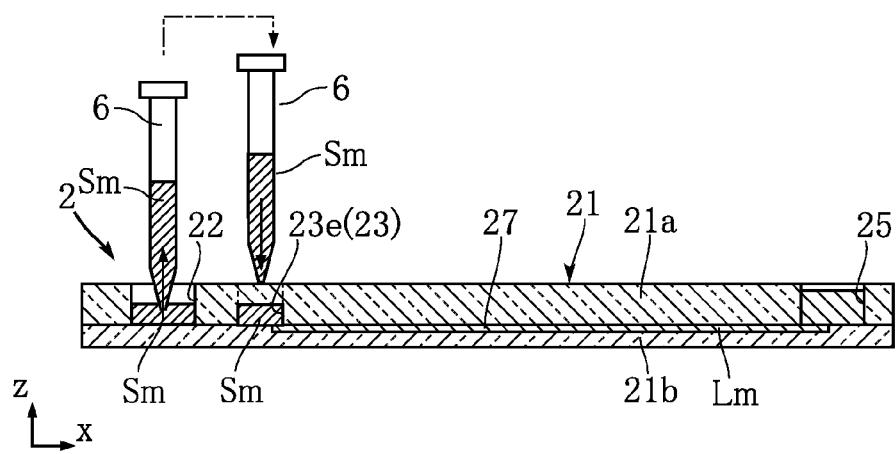
FIG. 10 is a cross-sectional view showing the analysis method in FIG. 6.
Figure 11:
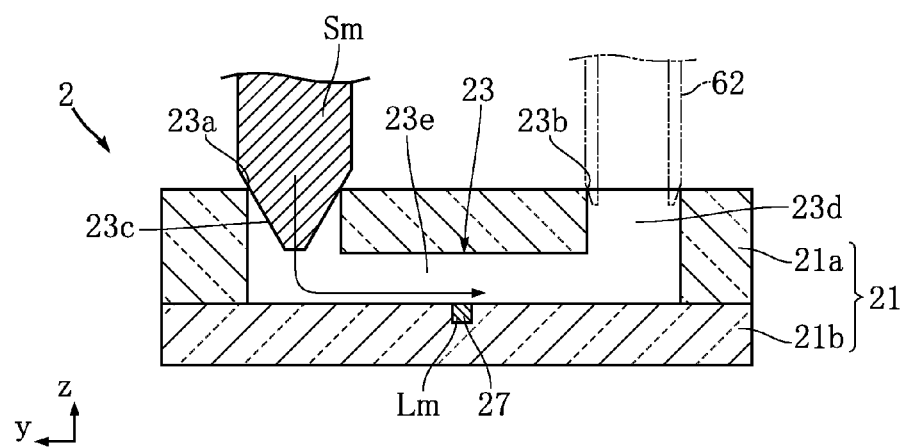
FIG. 11 is an enlarged cross-sectional view of the main portions showing the analysis method in FIG. 6.

Then, as shown in FIG. 10, a predetermined amount of mixed sample Sm is collected from the mixing tank 22 by the injector 6. Then, the predetermined amount of mixed sample Sm is introduced from the injector 6 to the introducing tank 23. In this introduction, the injector 6 is inserted into either the opening portion 23a or the opening portion 23b. In this example, as shown in FIG. 11, the injector 6 is inserted into the opening portion 23a. Furthermore, a nozzle 62 included in the analysis device 1 is linked to the opening portion 23b. The nozzle 62 is exposed to the atmosphere or is linked to the above-described flow drive source. When introduction of the mixed sample Sm from the injector 6 is started, air in the introducing tank 23 is discharged from the introducing tank 23 via the nozzle 62. At that time, the nozzle 62 may be exposed to the atmosphere, or may be provided with a suction force from a pump or the like as a flow drive source other than the pump 61 that provides the injector 6 with an ejection force.

Figure 12:
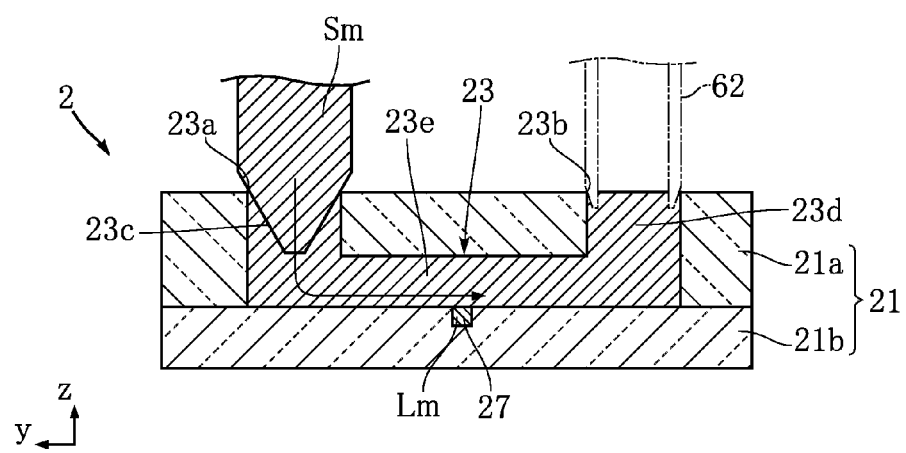
FIG. 12 is an enlarged cross-sectional view of the main portions showing the analysis method in FIG. 6.

FIG. 12 shows a state in which the introducing tank 23 is filled with the mixed sample Sm, and the introducing step S4 is completed. In this embodiment, a point in time when the introducing tank 23 is completely filled with the mixed sample Sm corresponds to a completion time of the introducing step S4. Note that, in the present invention, the point in time when the introducing step is completed is determined to be a point in time when introduction of a predetermined amount of sample necessary to perform the analysis step is completed, and is not necessarily determined to be a point in time when the introducing tank is completely filled with the sample.

<Flow Step S5>

Figure 13:
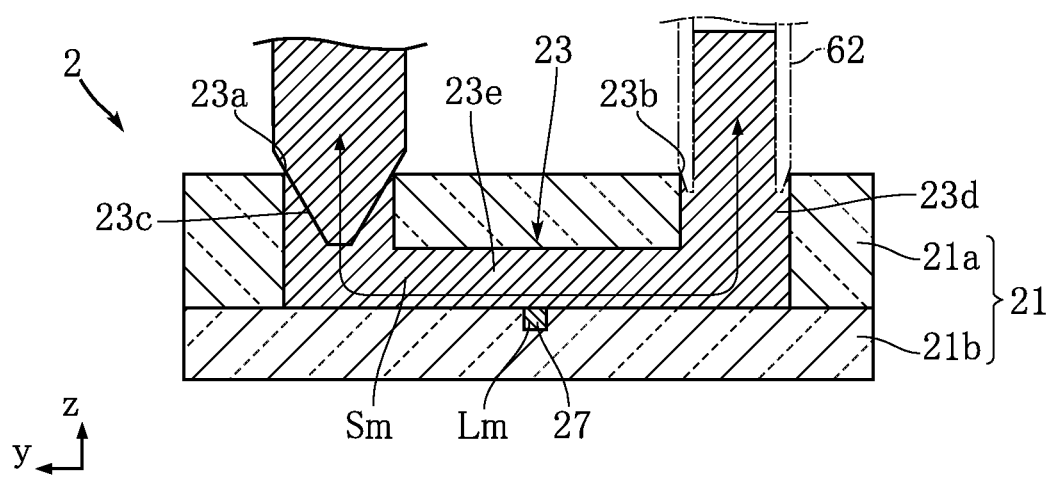
FIG. 13 is an enlarged cross-sectional view of the main portions showing the analysis method in FIG. 6.

Then, as shown in FIG. 13, the flow step S5 is performed. In this embodiment, after the completion time of the introducing step S4 shown in FIG. 12, the mixed sample Sm is repeatedly ejected from and sucked into the injector 6 using the pump 61 as the ejection source and the suction source, so that the mixed sample Sm is caused to flow inside the introducing tank 23. This flow is not a flow that is inevitably generated by the introduction of a predetermined amount of mixed sample Sm to the introducing tank 23 in the introducing step S4, but is a flow after the introduction of a predetermined amount of mixed sample Sm is completed. With this flow, a behavior is seen in which the mixed sample Sm moves back and forth mainly in the y direction in the lateral hole portion 23e of the introducing tank 23. That is to say, in a link portion between the lateral hole portion 23e of the introducing tank 23 and the capillary tube 27, the mixed sample Sm in the lateral hole portion 23e dominantly moves back and forth in the y direction and the electrophoretic liquid Lm in the capillary tube 27 hardly moves, so that a shear flow is generated. As a result, in the link portion between the lateral hole portion 23e and the capillary tube 27, a state is maintained in which a clear boundary between the mixed sample Sm and the electrophoretic liquid Lm is formed.

<Electrophoresis Step S6>

Then, as shown in FIG. 1, the electrode 31 is inserted into the introducing tank 23, and the electrode 32 is inserted into the discharging tank 25. Subsequently, in response to an instruction from the control portion 8, a voltage is applied to the electrode 31 and the electrode 32. This voltage is, for example, 0.5 kV to 20 kV. Accordingly, an electroosmotic flow is generated, so that the mixed sample Sm is gradually moved through the capillary tube 27 from the introducing tank 23 to the discharging tank 25. At that time, since the introducing tank 23 is filled with the mixed sample Sm, electrophoresis is performed in the capillary tube 27 in a state where the mixed sample Sm is continuously supplied. In this state, emission of light from the light source 41 is started, and the light absorbance is measured by the detector 5. Furthermore, a relationship between the period of time elapsed after the start of voltage application from the electrode 31 and the electrode 32 and the light absorbance is measured. A light absorbance peak corresponding to a component having a relatively high migration rate in the mixed sample Sm appears in a relatively short period of time elapsed after the start of voltage application. On the other hand, a light absorbance peak corresponding to a component having a relatively low migration rate in the mixed sample Sm appears in a relatively long period of time elapsed after the start of voltage application. Accordingly, an analysis (measurement by separation) of components in the mixed sample Sm is performed. The measured light absorbance is subjected to arithmetic processing (e.g., differential processing, difference processing, etc. by the control portion 8), so that an electropherogram is obtained. The component ratio and the like in the mixed sample Sm are obtained by calculating a peak height or a peak area of this electropherogram.

Next, examples of this analysis method will be described.

EXAMPLE 1

As the sample Sa, 95 µL of whole blood collected from a human body was used. As the diluting liquid Ld, a liquid prepared using 40 mM citric acid, 1.0% (w/v) chondroitin sulfate C-sodium, 500 mM NDSB-201 (manufactured by Anatarace), 0.1% (w/v) LS-110 (manufactured by Kao Corporation), and 0.1% (w/v) sodium azide and having a pH adjusted to 6.0 using dimethylaminoethanol (for pH adjustment) was used. As the electrophoretic liquid Lm, a liquid prepared using 40 mM citric acid, 1.25% (w/v) chondroitin sulfate C-sodium, 0.1% (w/v) LS-110 (manufactured by Kao Corporation), and 0.1% (w/v) sodium azide and having a pH adjusted to 5.0 using dimethylaminoethanol (for pH adjustment) was used.

As the analysis chip 2, an introducing tank 23 having a capacity of 20 μL, a discharging tank 25 having a capacity of 10 μL, and a capillary tube 27 having a width of 40 μm, a depth of 40 μm, and a total length of 30 mm (separation length 20 mm) were prepared. The inner wall of the capillary tube 27 was coated by poly(diallyldimethylammoniumchloride) (PDADMAC: manufactured by Sigma).

In the mixing step S2, the sample Sa was diluted 41 times with the diluting liquid Ld, so that a mixed sample Sm was obtained. The amount of electrophoretic liquid Lm filled in the electrophoretic liquid filling step S3 was 9 μL. In the introducing step S4, 18 μL of mixed sample Sm was introduced. In the flow step S5, ejection and suction by the injector 6 was repeated a plurality of times. In the electrophoresis step S6, the electrode 31 and the electrode 32 had a voltage of 0.5 kV to 20 kV and a current of 76 μA. With the detector 5, the light absorbance at a wavelength of 415 nm was measured, so that the electropherogram was obtained.

COMPARATIVE EXAMPLE

Measurement was performed as in Example 1, except that the flow step S5 was not performed. In this case, an analysis chip was used including a conventional introducing tank having only one opening portion, contrary to the introducing tank 23 of the analysis chip 2.

Figure 14:
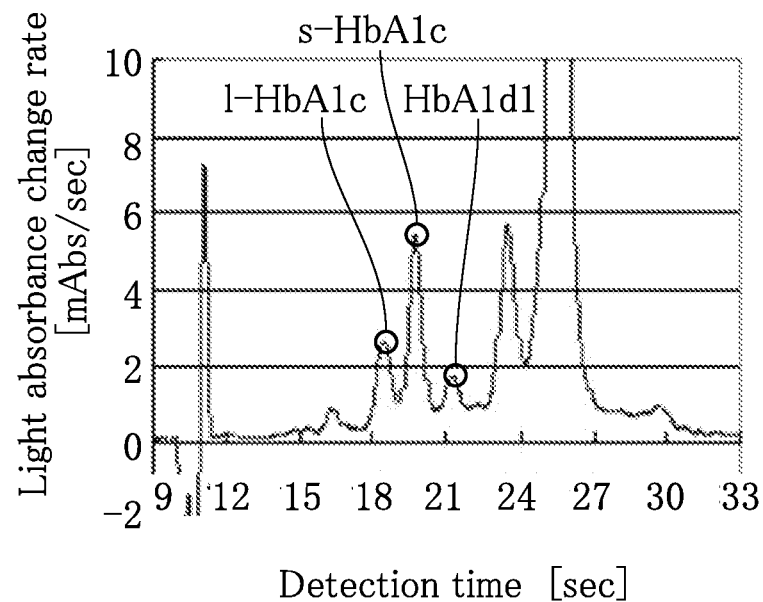
FIG. 14 is an electropherogram showing a result of an example of the analysis method in FIG. 6.
Figure 15:
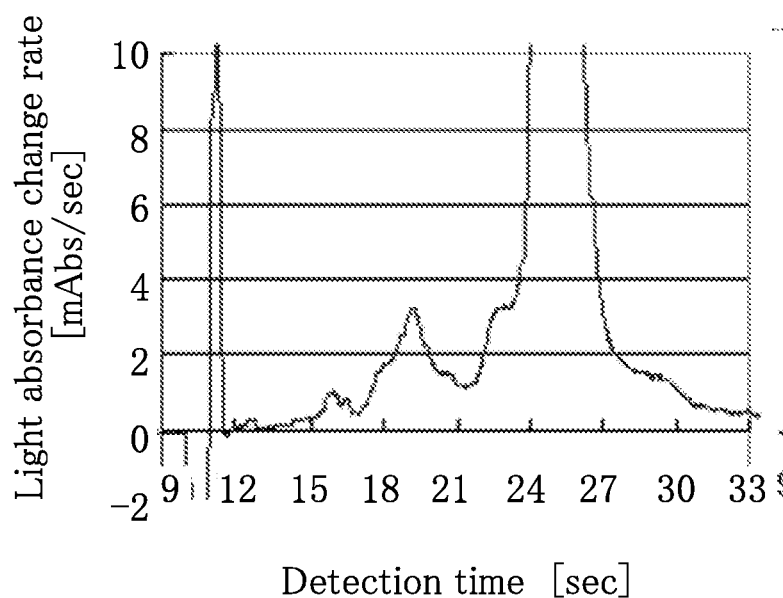
FIG. 15 is an electropherogram showing a result of a reference example of an analysis method.

FIG. 14 shows the electropherogram obtained in Example 1, and FIG. 15 shows the electropherogram obtained in Comparative Example. In these electropherograms, the horizontal axis indicates a detection time (unit: sec), and the vertical axis indicates a light absorbance change rate (unit: mAbs/sec).

Next, the actions of the analysis chip 2, the analysis system A1, and this analysis method will be described.

As shown in FIG. 14, in the electropherogram in Example 1, peaks of the analysis components l-HbA1c, s-HbA1c, and HbA1d1 individually and clearly appear at different times. On the other hand, as shown in FIG. 15, in the electropherogram in Comparative Example, peaks of the analysis components l-HbA1c, s-HbA1c, and HbA1d1 do not clearly appear as individual peaks. According to experiments by the inventors, it was found that clear peaks do not appear because the electrophoretic liquid Lm in the capillary tube 27 leaks into the introducing tank 23, for example, before, during, or directly after the introducing step S4, in the link portion between the introducing tank 23 and the capillary tube 27. That is to say, if the electrophoretic liquid Lm leaks into the introducing tank 23, not the pure mixed sample Sm but a mixed sample Sm diluted with the electrophoretic liquid Lm may be retained in the portion of the introducing tank 23 linked to the capillary tube 27. Also, the electrophoretic liquid Lm that leaked before the introducing step S4 may be evaporated to dryness near the portion of the introducing tank 23 linked to the capillary tube 27, forming a region in which the components of the electrophoretic liquid Lm are concentrated, and, thus, during the introducing step S4, the mixed sample Sm excessively containing the components of the electrophoretic liquid Lm may be retained in that link portion. Also, the electrophoretic liquid Lm and the mixed sample Sm may be mutually diffused, forming a region having an unclear component ratio of the mixed sample Sm. When the electrophoresis step S6 is started, the mixed sample Sm that is undesirably diluted, that excessively contains the components of the electrophoretic liquid Lm, or that has an unclear component ratio is analyzed, so that the precision of the analysis result is significantly lowered. On the other hand, in Example 1, the flow step S5 is performed, so that a clear boundary between the mixed sample Sm and the electrophoretic liquid Lm is formed in the link portion between the introducing tank 23 and the capillary tube 27. In other words, even when the electrophoretic liquid Lm in the capillary tube 27 leaks into the introducing tank 23, the mixed sample Sm that is diluted, that excessively contains the components of the electrophoretic liquid Lm, or that has an unclear component ratio is washed away with a shear flow in the flow step S5. As a result, the pure mixed sample Sm suitable for the intended analysis can be present at the link portion between the introducing tank 23 and the capillary tube 27. Accordingly, clear peaks of the analysis components can be obtained as shown in FIG. 14, and the analysis precision can be improved with a simpler configuration.

The configuration in which the two opening portions 23a and 23b are used as the flow means and the mixed sample Sm is caused to flow between the opening portions 23a and 23b can be realized by performing the flow step S5 using the injector 6, which is a mechanism for introducing the mixed sample Sm to the introducing tank 23. This aspect is suitable for preventing the configuration of the analysis system A1 from being complicated. In particular, if the two opening portions 23a and 23b are opened in the same direction, it is possible to arrange the injector 6 and the nozzle 62 in the same direction with respect to the analysis chip 2 when setting the analysis chip 2 in the analysis device 1. This aspect is preferable for reducing the size of the analysis device 1, for example.

Since the dimensions in the x direction and in the y direction of the introducing tank 23 are larger than the dimensions in the x direction and in the y direction of the opening portion of the capillary tube 27, in the flow step S5, the mixed sample Sm can be caused to actively flow inside the introducing tank 23, and the electrophoretic liquid Lm in the capillary tube 27 can be retained inside the capillary tube 27 without being caused to flow to the extent possible. This aspect is advantageous for forming a clearer boundary between the mixed sample Sm and the electrophoretic liquid Lm, in the link portion between the introducing tank 23 and the capillary tube 27.

Figure 16:
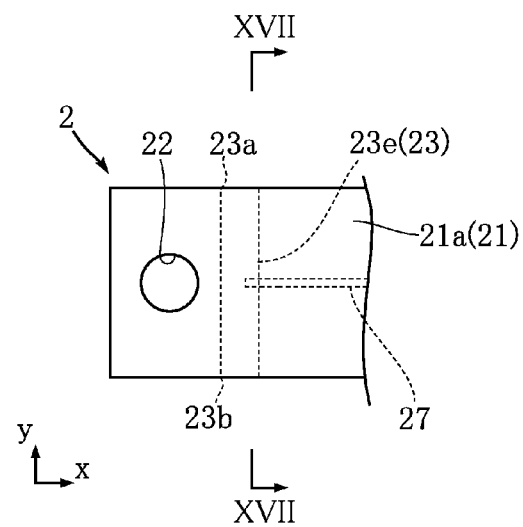
FIG. 16 is a plan view of the main portions showing another example of the analysis chip according to the present invention.
Figure 17:
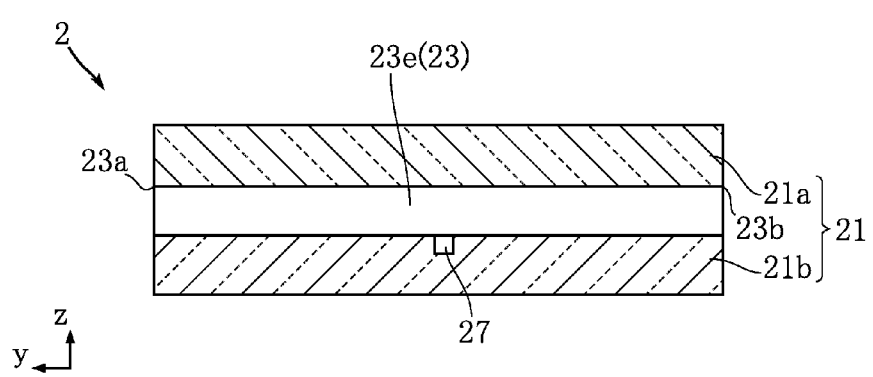
FIG. 17 is a cross-sectional view taken along the line XVII-XVII in FIG. 16.

FIGS. 16 and 17 show another example of the analysis chip 2. In this example, the opening portion 23a and the opening portion 23b are opened in different directions. In FIG. 16, the opening portion 23a is opened in the direction of the arrow in the y direction in the drawing, and the opening portion 23b is opened in the direction opposite from the arrow in the y direction in the drawing. Furthermore, the introducing tank 23 is configured only by the lateral hole portion 23e that links the opening portion 23a and the opening portion 23b. As shown in FIG. 17, also in this example, the capillary tube 27 is linked to a portion near the middle of the lateral hole portion 23e. Furthermore, the dimensions in the x direction and in the y direction of the lateral hole portion 23e are larger than the dimensions in the x direction and in the y direction of the opening portion of the capillary tube 27. In the analysis device 1 in which the thus configured analysis chip 2 is set, the injector 6 and the nozzle 62 having different orientations and different shapes from those of the injector 6 and the nozzle 62 described above are used as appropriate.

Also in this example, the analysis precision can be improved with a simpler configuration. Furthermore, the two opening portions 23*a* and 23*b* may be opened in different directions. For example, one of the opening portions 23*a* and 23*b* may be opened in the z direction, and the other opening portion may be opened in the y direction. Alternatively, the opening portions 23*a* and 23*b* may be opened in opposite directions in the z direction.

Furthermore, not only the introducing tank 23 but also the discharging tank 25 may have two opening portions. In this case, for example, in addition to the use method that defines the introducing tank 23 and the discharging tank 25 respectively as dedicated tanks, a use method that uses the introducing tank 23 and the discharging tank 25 in an interchangeable manner can be used.

Figure 18:
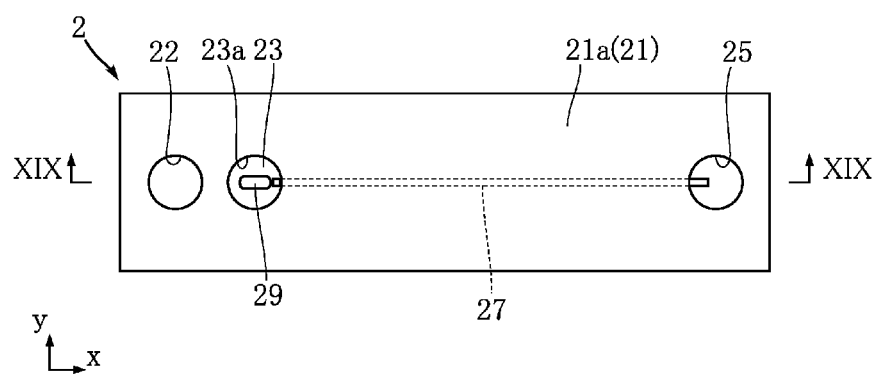
FIG. 18 is a plan view of the main portions showing another example of the analysis chip according to the present invention.
Figure 19:
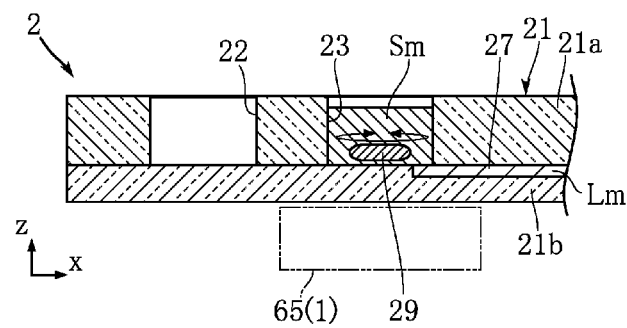
FIG. 19 is a cross-sectional view taken along the line XIX-XIX in FIG. 18.

FIGS. 18 and 19 show another example of the analysis chip 2. In this example, the introducing tank 23 accommodates a stirrer piece 29. The introducing tank 23 of this example has only one opening portion 23*a*. The stirrer piece 29 is made of, for example, a magnetic material (e.g., Fe) coated by an insulating material (e.g. resin), and corresponds to an example of the flow means in the present invention.

FIG. 19 shows a state in which the analysis chip 2 is set in the analysis device 1 and the flow step S5 is being performed. The analysis device 1 used in this example includes a magnetic drive source 65. The magnetic drive source 65 generates a magnetic force that can rotate the stirrer piece 29 of the analysis chip 2 disposed near the magnetic drive source 65. When a predetermined amount of mixed sample Sm is introduced to the introducing tank 23, the introducing step S4 is ended. As shown in the drawing, in this example, the predetermined amount of mixed sample Sm that is to be introduced is slightly smaller than the total capacity of the introducing tank 23. In the flow step S5, the stirrer piece 29 is rotated inside the introducing tank 23 by the magnetic drive source 65. Accordingly, a rotational flow of the mixed sample Sm is generated in the introducing tank 23, and a shear flow that forms a clear boundary between the mixed sample Sm and the electrophoretic liquid Lm is generated in the link portion between the introducing tank 23 and the capillary tube 27. Also in this example, the analysis precision can be improved with a simpler configuration.

The analysis method, the analysis chip, and the analysis system according to the present invention are not limited to the foregoing embodiment. The specific configuration of the analysis method, the analysis chip, and the analysis system according to the present invention can be variously designed and modified.

The invention claimed is:

1. A method for analyzing a sample using an analysis chip for capillary electrophoresis, the method comprising:
    filling a capillary tube with an electrophoretic liquid, wherein the capillary tube links an introducing tank and a discharging tank, the introducing tank is provided with a lateral hole portion that has a first opening portion and a second opening portion at both ends of the lateral hole portion, the lateral hole portion has a link portion where a third opening portion at one end of the capillary tube is linked to the lateral hole portion, and a cross-section of the link portion is larger than that of the third opening portion;
    leaking the electrophoretic liquid into the introducing tank in a state in which the capillary tube has been filled with the electrophoretic liquid, then introducing a predetermined amount of the sample into the introducing tank;
    after introducing the predetermined amount of the sample into the introducing tank, causing the sample to flow, in the introducing tank, so that the sample traverses the capillary tube at the link portion between the introducing tank and the capillary tube, with use of a pump so that a shear flow is generated at the link portion to create a clear boundary between the sample and the electrophoretic liquid;
    after the sample traverses the capillary tube at the link portion, performing electrophoresis in the capillary tube while the sample is continuously supplied into the introducing tank.

2. The analysis method according to claim 1, wherein the sample is poured into and discharged from the two opening portions.

3. The analysis method according to claim 1, wherein the electrophoresis is performed by applying a voltage to an electrode inserted into the introducing tank.

\* \* \* \* \*